(12) United States Patent
Hodorek

(10) Patent No.: US 11,918,473 B2
(45) Date of Patent: *Mar. 5, 2024

(54) SURGICAL INSTRUMENTATION ASSEMBLY, SET AND SURGICAL SHOULDER REPAIR METHOD

(71) Applicant: HOWMEDICA OSTEONICS CORP., Mahwah, NJ (US)

(72) Inventor: Brian C. Hodorek, Winona Lake, IN (US)

(73) Assignee: HOWMEDICA OSTEONICS CORP., Mahwah, NJ (US)

( * ) Notice: Subject to any disclaimer, the term of this patent is extended or adjusted under 35 U.S.C. 154(b) by 185 days.

This patent is subject to a terminal disclaimer.

(21) Appl. No.: 17/378,910

(22) Filed: Jul. 19, 2021

(65) Prior Publication Data
US 2021/0338435 A1    Nov. 4, 2021

Related U.S. Application Data

(62) Division of application No. 15/454,259, filed on Mar. 9, 2017, now Pat. No. 11,090,161.

(Continued)

(51) Int. Cl.
*A61F 2/40* (2006.01)
*A61B 17/16* (2006.01)
(Continued)

(52) U.S. Cl.
CPC ...... *A61F 2/30767* (2013.01); *A61B 17/1604* (2013.01); *A61F 2/4081* (2013.01);
(Continued)

(58) Field of Classification Search
None
See application file for complete search history.

(56) References Cited

U.S. PATENT DOCUMENTS

| | | | |
|---|---|---|---|
| 4,659,331 A * | 4/1987 | Matthews | A61F 2/38 D24/155 |
| 5,098,383 A * | 3/1992 | Hemmy | A61M 5/427 604/116 |

(Continued)

FOREIGN PATENT DOCUMENTS

WO    WO-2011135377 A1 *  11/2011   ......... A61F 2/30771

OTHER PUBLICATIONS

European Search Report issued in connection with European Patent Application No. 17770941.7, dated Oct. 29, 2019, 6 pages.

(Continued)

*Primary Examiner* — Ann Schillinger
(74) *Attorney, Agent, or Firm* — DUANE MORRIS LLP

(57) ABSTRACT

This surgical instrumentation assembly is for positioning a shoulder prosthesis, the shoulder prosthesis comprising a patient-specific shoulder implant adapted to fit onto a glenoid cavity of the scapula of a patient. The assembly comprises a patient-specific impacting device having an underside surface congruent with the glenoid cavity of the scapula of the patient, said underside surface being provided with protrusions adapted to perforate the cortical bone of the scapula upon impact of the impacting device against the scapula by a one-sided translation movement.

12 Claims, 4 Drawing Sheets

Related U.S. Application Data

(60) Provisional application No. 62/313,470, filed on Mar. 25, 2016.

(51) Int. Cl.
   *A61B 17/17* (2006.01)
   *A61B 17/88* (2006.01)
   *A61B 90/00* (2016.01)
   *A61F 2/30* (2006.01)
   *A61B 17/86* (2006.01)

(52) U.S. Cl.
   CPC .......... *A61B 17/1778* (2016.11); *A61B 17/86* (2013.01); *A61F 2002/3092* (2013.01); *A61F 2/30942* (2013.01); *A61F 2220/0016* (2013.01)

(56) References Cited

U.S. PATENT DOCUMENTS

| | | | |
|---|---|---|---|
| 5,885,298 A | 3/1999 | Herrington et al. | |
| 5,895,178 A * | 4/1999 | Young | B23B 51/0453 |
| | | | 409/206 |
| 5,961,535 A | 10/1999 | Rosenberg | |
| 6,059,789 A * | 5/2000 | Dinger | A61B 17/0483 |
| | | | 606/86 R |
| 9,248,022 B2 | 2/2016 | Lappin | |
| 9,700,325 B2 | 7/2017 | Schoenefeld | |
| 11,090,161 B2 * | 8/2021 | Hodorek | A61F 2/30767 |
| 11,344,422 B2 * | 5/2022 | Maale | A61F 2/4081 |
| 2005/0043805 A1 * | 2/2005 | Chudik | A61B 17/1684 |
| | | | 623/908 |
| 2005/0060039 A1 * | 3/2005 | Cyprien | A61F 2/30771 |
| | | | 623/19.13 |
| 2005/0245934 A1 * | 11/2005 | Tuke | A61B 17/175 |
| | | | 606/79 |
| 2006/0122616 A1 * | 6/2006 | Bennett | A61B 17/1764 |
| | | | 606/87 |
| 2006/0195194 A1 | 8/2006 | Gunther | |
| 2006/0271058 A1 * | 11/2006 | Ashton | A61B 17/175 |
| | | | 606/96 |
| 2008/0114370 A1 * | 5/2008 | Schoenefeld | A61B 17/1721 |
| | | | 606/96 |
| 2009/0105772 A1 * | 4/2009 | Seebeck | A61F 2/30771 |
| | | | 606/328 |
| 2009/0239195 A1 * | 9/2009 | Wohrle | A61C 8/0077 |
| | | | 433/174 |
| 2011/0029088 A1 * | 2/2011 | Rauscher | A61B 17/1778 |
| | | | 623/19.11 |
| 2011/0035013 A1 * | 2/2011 | Winslow | A61F 2/4081 |
| | | | 623/19.13 |
| 2011/0166578 A1 | 7/2011 | Stone et al. | |
| 2012/0046663 A1 | 2/2012 | Shimko | |
| 2013/0006250 A1 | 1/2013 | Metzger et al. | |
| 2013/0245631 A1 * | 9/2013 | Bettenga | A61B 17/1746 |
| | | | 606/91 |
| 2013/0261629 A1 * | 10/2013 | Anthony | A61B 17/16 |
| | | | 606/80 |
| 2014/0107715 A1 | 4/2014 | Heilman et al. | |
| 2014/0257499 A1 | 9/2014 | Winslow et al. | |
| 2014/0276856 A1 * | 9/2014 | Schoenefeld | A61B 34/10 |
| | | | 606/87 |
| 2015/0150688 A1 | 6/2015 | Vanesse | |
| 2015/0265292 A1 * | 9/2015 | Olson | A61B 17/1684 |
| | | | 606/80 |
| 2016/0045323 A1 | 2/2016 | Kovacs et al. | |
| 2016/0374693 A1 * | 12/2016 | Van Citters | A61F 2/4684 |
| | | | 606/88 |

OTHER PUBLICATIONS

Search Report and Written Opinion issued in PCT/US2017/02305 dated Jun. 30, 2017 (12 pages).

* cited by examiner

SURGICAL INSTRUMENTATION ASSEMBLY, SET AND SURGICAL SHOULDER REPAIR METHOD

CROSS-REFERENCE TO RELATED APPLICATIONS

This is a divisional application of co-pending U.S. patent application Ser. No. 15/454,259, filed on Mar. 9, 2017, which claims priority to U.S. Provisional Application No. 62/313,470, filed on Mar. 25, 2016 the disclosures of which are incorporated by reference herein in their entireties.

FIELD

The invention concerns a surgical instrumentation assembly for positioning a shoulder prosthesis. The invention also concerns a set comprising a shoulder implant and such a surgical instrumentation assembly. The invention also concerns a surgical shoulder repair method.

BACKGROUND

Surgical shoulder repair methods using conventional base plates require much instrumentation to conform the bone of the patient to the implant. The preparation of the bone requires reaming, which is difficult to implement due to the exposition of the bone, and several types of implants require extensive reaming resulting in bone loss, or require special bone augments and corresponding instrumentations to provide enough support for the base plates of the implant. These methods need much instrumentation and time.

It is known to use patient-specific implants and instrumentation which directly fit the shape of the bone of the patient. The instrumentation and the implants are designed using medical imaging technology such as CT scans, X-rays, MRI or the like.

However when using patient specific implants, which are directly fixed on the cortical bone of the glenoid cavity of the patient, the secondary anchoring, which is provided by bone growth, is much less efficient because the cortical bone does not facilitate bone growth. The anchoring of the implant therefore only relies on a mechanical anchoring provided by posts and screws.

SUMMARY

The aim of the invention is to provide a new surgical instrumentation assembly, set and surgical shoulder repair method which provides a better anchoring for patient specific implants.

To this end, the invention concerns a surgical instrumentation assembly for positioning a shoulder prosthesis, the shoulder prosthesis comprising a patient-specific shoulder implant adapted to fit onto a glenoid cavity of the scapula of a patient, wherein the assembly comprises a patient-specific impacting device having an underside surface congruent with the glenoid cavity of the scapula of the patient, said underside surface being provided with protrusions adapted to perforate the cortical bone of the scapula upon impact of the impacting device against the scapula by a one-sided translation movement.

Thanks to the invention, the perforations made in the cortical bone facilitate bone growth induced by the cancellous bone, which is allowed to expand towards the surface of the implant. The secondary anchoring of the implant is therefore improved.

According to further aspects of the invention which are advantageous but not compulsory, such a surgical instrumentation assembly may include one or several of the following features:

The protrusions of the impacting device are adapted to create channels in the cortical bone of the scapula, the channels extending towards the cancellous bone of the scapula.

The protrusions have a distribution and a shape arranged according to different densities, thicknesses and lengths determined on the basis of the density and thickness of the cortical bone of the glenoid cavity of the scapula of the patient.

The impacting device comprises a post adapted to be inserted into a positioning hole drilled in the scapula.

The assembly comprises a patient specific drilling guide for drilling holes for inserting a post of a shoulder implant and a screw for attaching the shoulder implant.

The drilling guide comprises a notch for positioning a reference marker on the scapula.

The impacting device comprises a notch for alignment with a reference marker.

The protrusions are spikes.

The invention also concerns a set comprising a shoulder implant and a surgical instrumentation assembly as mentioned here-above, wherein the shoulder implant comprises a porous underside portion which bears a surface congruent with the surface of the glenoid cavity.

The invention also concerns a surgical instrumentation assembly for positioning a shoulder prosthesis, the shoulder prosthesis comprising a patient-specific shoulder implant adapted to fit onto a glenoid cavity of the scapula of a patient, wherein the assembly comprises a patient-specific impacting device having an underside surface which is a negative surface of the glenoid cavity of the scapula of the patient, said underside surface being provided with protrusions adapted to perforate the cortical bone of the scapula.

According to an advantageous embodiment, the impacting device provides a one-sided translation movement with respect to the scapula.

The invention also concerns a surgical shoulder repair method comprising the steps of:

a) providing a patient specific impacting device having an underside surface congruent with the surface of the glenoid cavity of the scapula of the patient, said underside surface being provided with protrusions adapted to perforate the cortical bone of the scapula upon impact of the impacting device by a one-sided translation movement;

b) impacting the glenoid cavity to create channels through the cortical bone of the scapula;

c) providing a patient specific shoulder implant having an underside portion made of a porous material adapted to facilitate bone growth induced by the channels created through the cortical bone.

The combination of the perforations of the cortical bone and the porous properties of the underside portion of the implant allows bone growth in the porosities of the implant, thus improving the secondary anchoring of the implant in the scapula of the patient.

According to further aspects of the invention which are advantageous but not compulsory, such a surgical shoulder repair method may incorporate one or several of the following features:

The method comprises prior to step a), further steps consisting in:

d) providing a patient-specific drilling guide having an underside surface congruent with the surface of the glenoid cavity of the scapula of a patient;

e) drilling holes for a post of the shoulder implant and a screw for attachment of the shoulder implant.

The lengths of the post and screw are pre-determined.

The method comprises a further step consisting in providing a notch in the drilling guide for placing a reference marker on the scapula.

The distribution and shape of the protrusions are determined by imaging technology on the basis of the bone characteristics of the glenoid cavity of the scapula of the patient.

The density, the thickness and the length of the protrusions are determined depending on the density and thickness of the cortical bone of the glenoid cavity measured by CT scans.

Thinner and longer protrusions are used where the cortical bone is thicker.

The method comprises a step consisting in aligning the impacting device with a reference marker provided on the scapula.

The method comprises a step consisting in providing a notch in the impacting device for alignment with the reference marker.

BRIEF DESCRIPTION OF THE DRAWINGS

The invention will now be explained in reference to the annexed drawings, as an illustrative example. In the annexed drawings.

DETAILED DESCRIPTION

Figure 1:
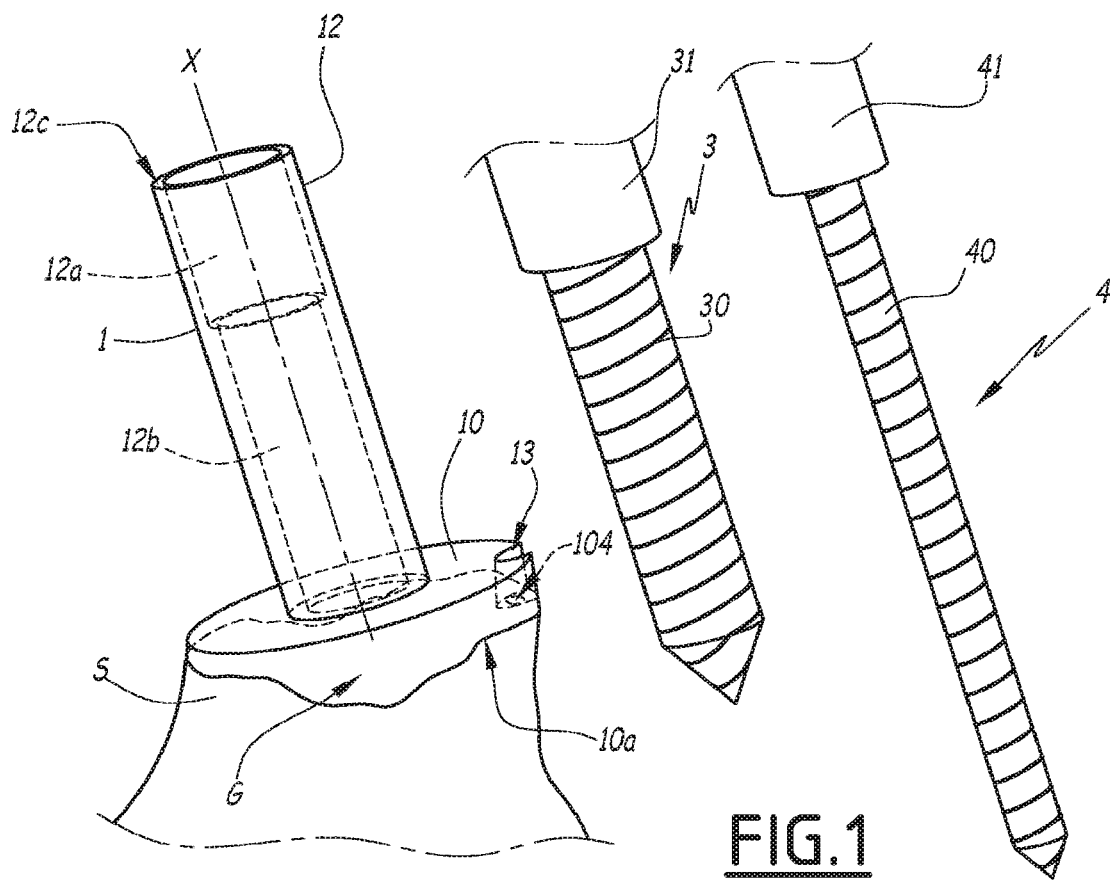
FIG. 1 is a perspective view of a drilling guide and drilling tools belonging to a surgical instrumentation assembly according to the invention.
Figure 4:
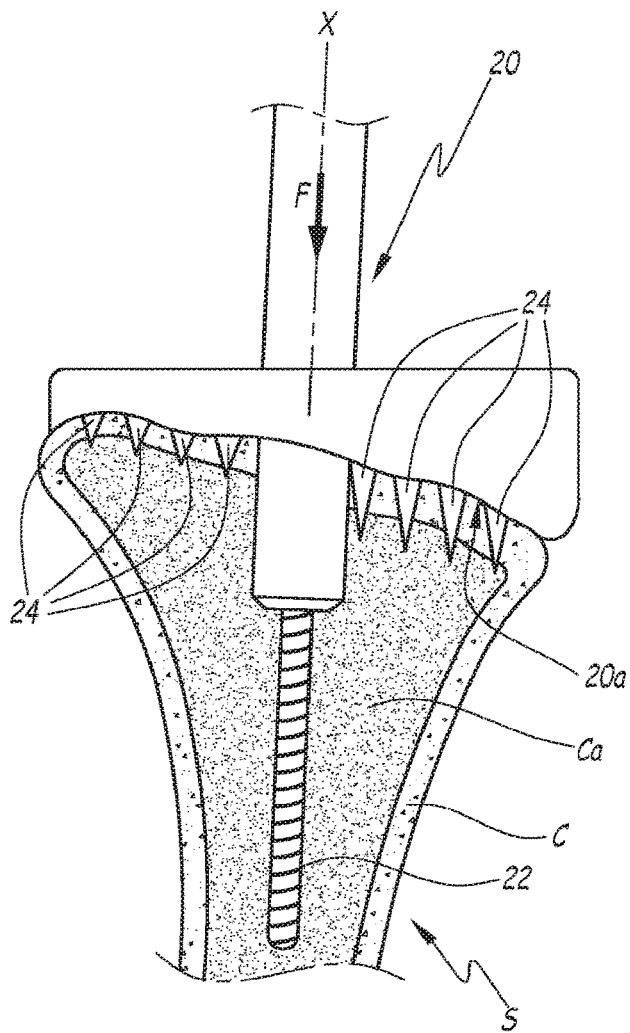
FIG. 4 is a sectional view of the scapula and impacting device of FIG. 3 during impact.

FIG. 1 shows a scapula S of a patient, the scapula S comprising a glenoid cavity G. The glenoid cavity G shows a damaged irregular surface which motivates the attachment of an implant. The scapula S comprises a cortical bone area C, which is the outer and hard bone portion of the scapula S. The scapula S also comprises a cancellous bone area Ca, which is the inner and soft bone portion of the scapula S. The cortical bone C and the cancellous bone Ca are represented on FIGS. 4 to 6.

FIG. 1 also represents a drilling guide 1. The drilling guide 1 is patient specific and comprises a base plate 10 having an underside surface 10a which is congruent to the glenoid cavity G. The drilling guide comprises a tube 12 for inserting drilling tools 3 and 4, which are used for drilling holes in the scapula S. The tube 12 is centered on a central axis X. The tube 12 comprises a first section 12a, whose diameter is adapted to receive a bit 30 of the drilling tool 3 and a stop element 41 of the drilling tool 4. The tube comprises a second section 12b which has a reduced diameter adapted for insertion of the bit 30 and prevents further insertion of the stop element 41. The tube 12 comprises an axial edge 12c which prevents insertion of a stop element 31 of the drilling tool 3.

The axial dimensions of the sections 12a and 12b along the axis X are predetermined on the basis of the depth of a post and a screw used to attach a shoulder implant to the scapula S, which are patient-specific and determined using medical imaging technologies.

Figure 2:
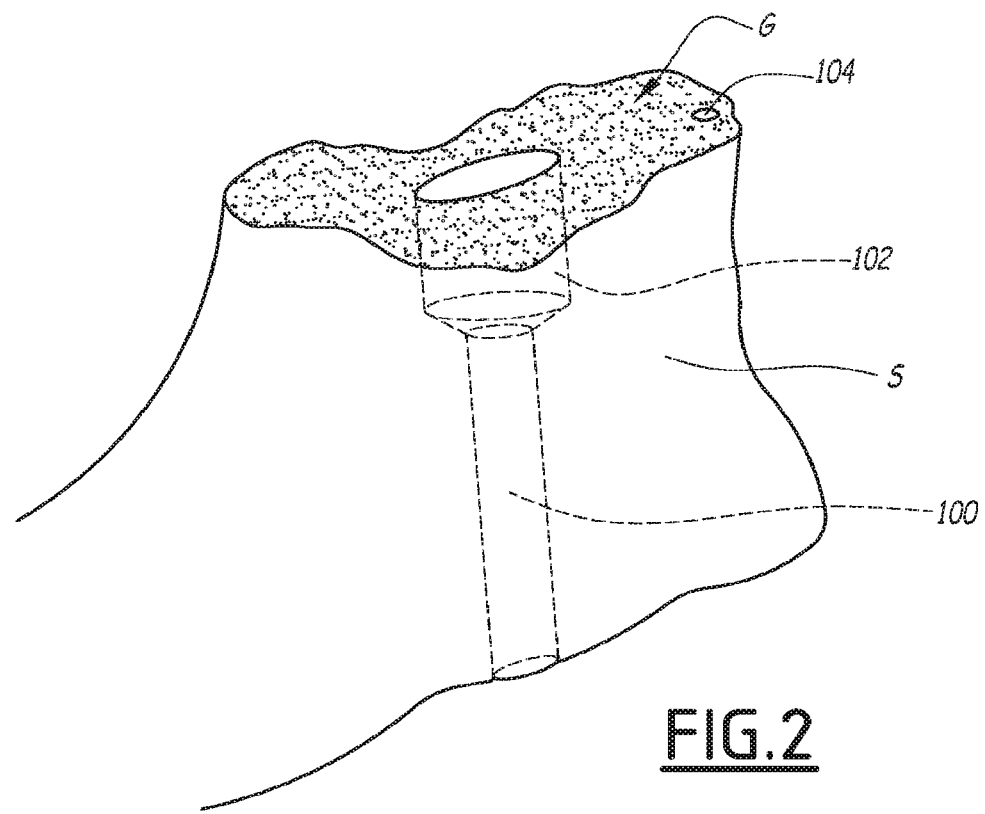
FIG. 2 is a perspective view of a scapula of a patient in which drillings have been performed using the surgical instrumentation assembly of FIG. 1.
Figure 3:
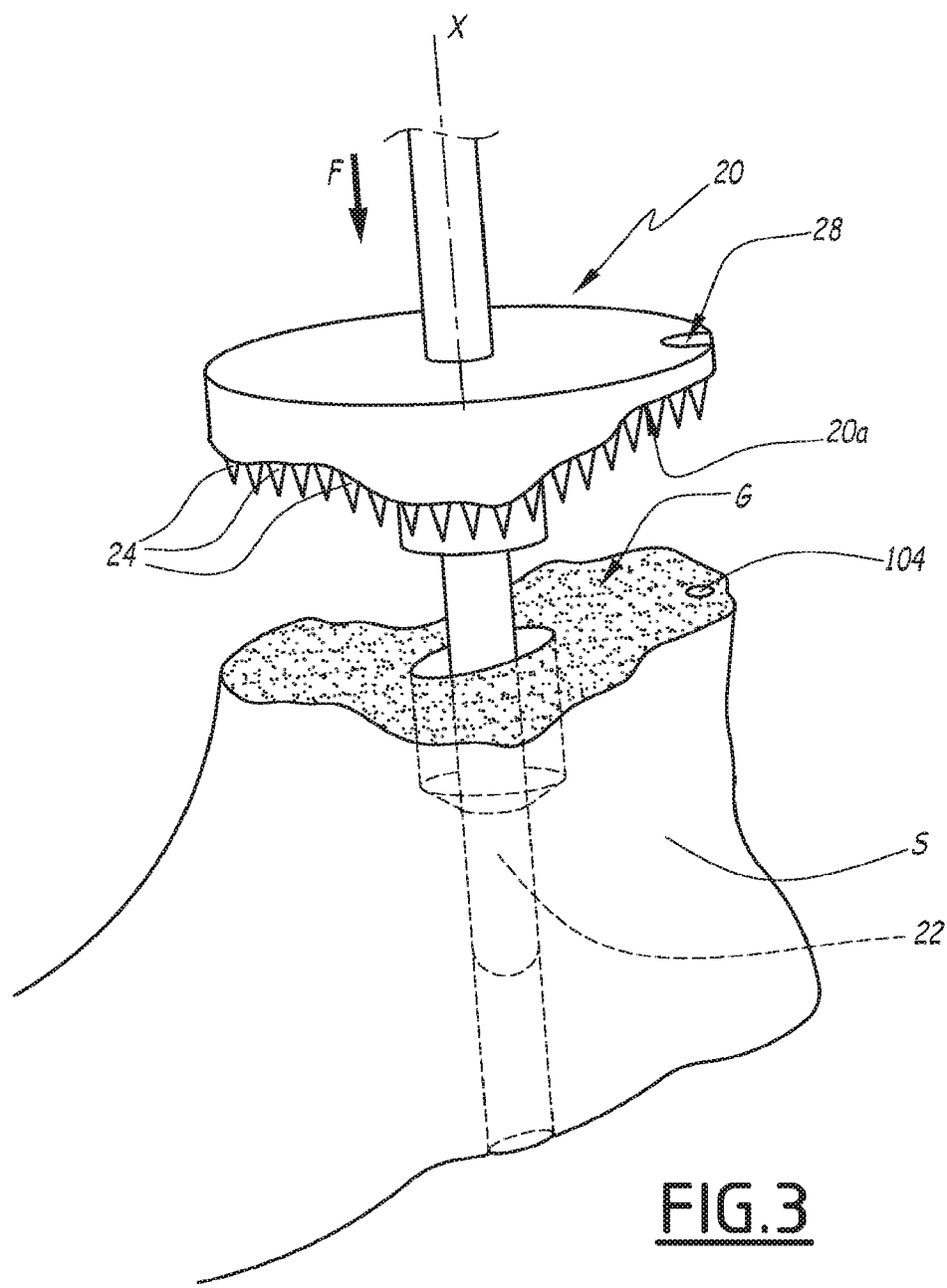
FIG. 3 is a perspective view of the scapula of FIG. 2, in which is inserted an impacting device belonging to the surgical instrumentation assembly according to the invention.

On FIG. 2, the scapula S is represented after drillings have been performed. The scapula S shows a first hole 100, drilled by the drilling tool 4, and a second hole 102, which is coaxial and adjacent to the hole 100, and which is drilled by the drilling tool 3. The hole 100 is adapted for insertion of a screw, while the hole 102 is adapted for insertion of the post of the shoulder implant.

According to an optional feature, the drilling guide 1 comprises a positioning notch 13 provided on the base plate 10, and adapted to permit positioning of a reference marker. In the represented example, the reference marker is a hole 104 drilled in the scapula S. As a non-shown variant, the reference marker can be a pin, or the like.

The surgical instrumentation assembly also comprises an impacting device 20 having an underside surface 20a which is congruent to the surface of the glenoid cavity G. The underside surface 20a of the impacting device 20 is a negative surface of the glenoid cavity G.

The impacting device 20 comprises a post 22 made of two sections whose diameters fit the diameters of the holes 100 and 102.

The impacting device 20 comprises protrusions 24, formed by spikes in this example, which are provided on the underside surface and oriented along axis X towards the glenoid cavity G. The protrusions 24 form elongated elements protruding from the underside surface 20a along axis X. The protrusions 24 are adapted to perforate the cortical bone C upon impact of the impacting device 20 against the scapula S by a one sided translation movement, along axis X, as shown by arrow F.

Thanks to the orientation of the post 22 along axis X and to a rod 26 of the impacting device 20, which extends along axis X, and adapted to be handled by a physician, the impacting device 20 provides a one sided translation movement with respect to the scapula S.

Figure 5:
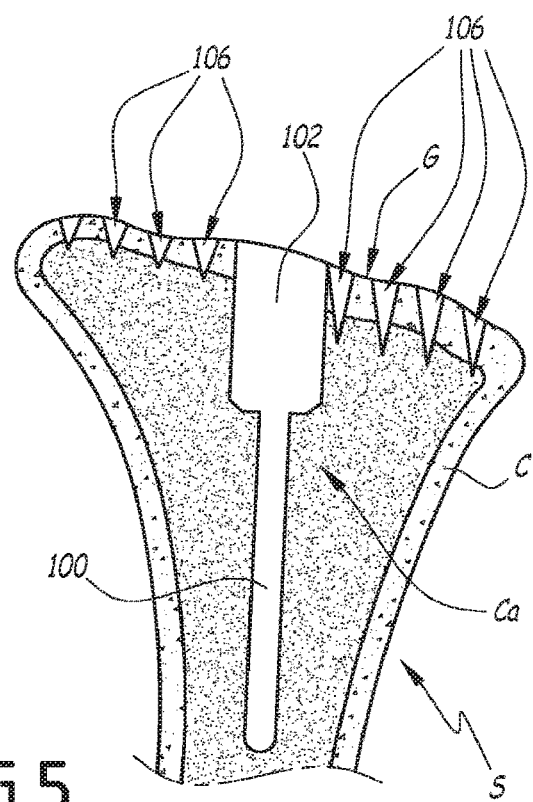
FIG. 5 is a sectional view of the scapula after impact and withdrawal of the impacting device.

As represented on FIG. 5, the protrusions 24 are adapted to create channels 106 in the cortical bone C. The channels 106 extend towards the cancellous bone Ca.

The shape and spatial distribution of the protrusions 24 is arranged according to different densities, thicknesses and lengths determined on the basis of the density and the thickness of the cortical bone C. Depending on the properties of the cortical bone C, which are determined using imaging, such as CT scans, the shape and distribution of protrusions 24 is determined so that the cortical bone C is properly perforated during impaction of the impacting device 20.

The length of the protrusions 24 can be comprised between 1 and 5 millimeters depending on the thickness of the cortical bone C.

The thickness of the protrusions 24 can be comprised between 0.5 and 3 millimeters depending on the hardness or density of the cortical bone C.

The density of the protrusions 24 can be comprised between 1 and 10 protrusions per square centimeter depending on the hardness or density of the cortical bone C.

The protrusions 24 are arranged and shaped so that thinner and longer protrusions 24 are used where the cortical bone is thicker.

The impacting device 20 comprises a notch 28 adapted to be aligned with the reference hole 104 provided on the glenoid cavity G.

Figure 6:
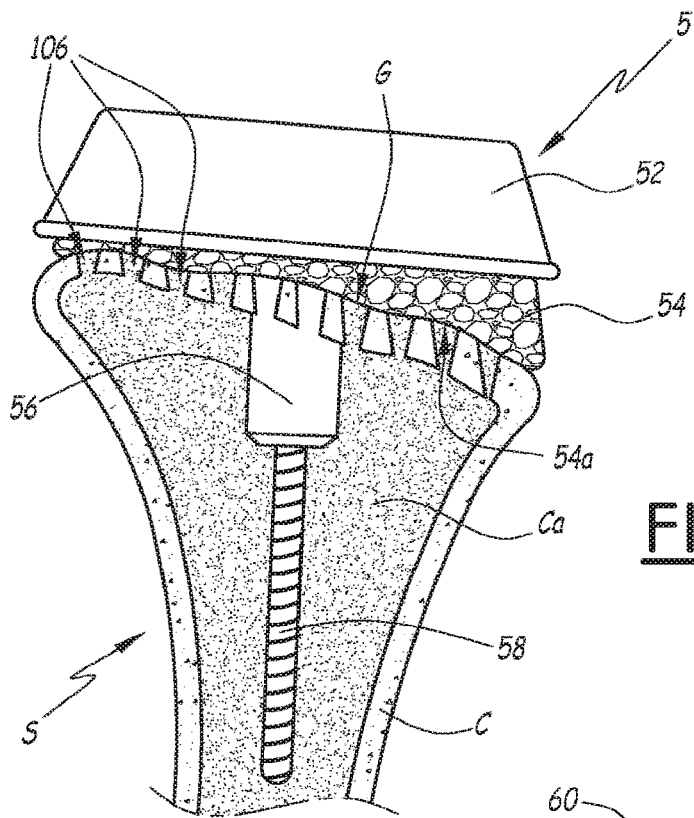
FIG. 6 is a sectional view of the scapula, and of a shoulder implant fixed to the scapula.
Figure 7:
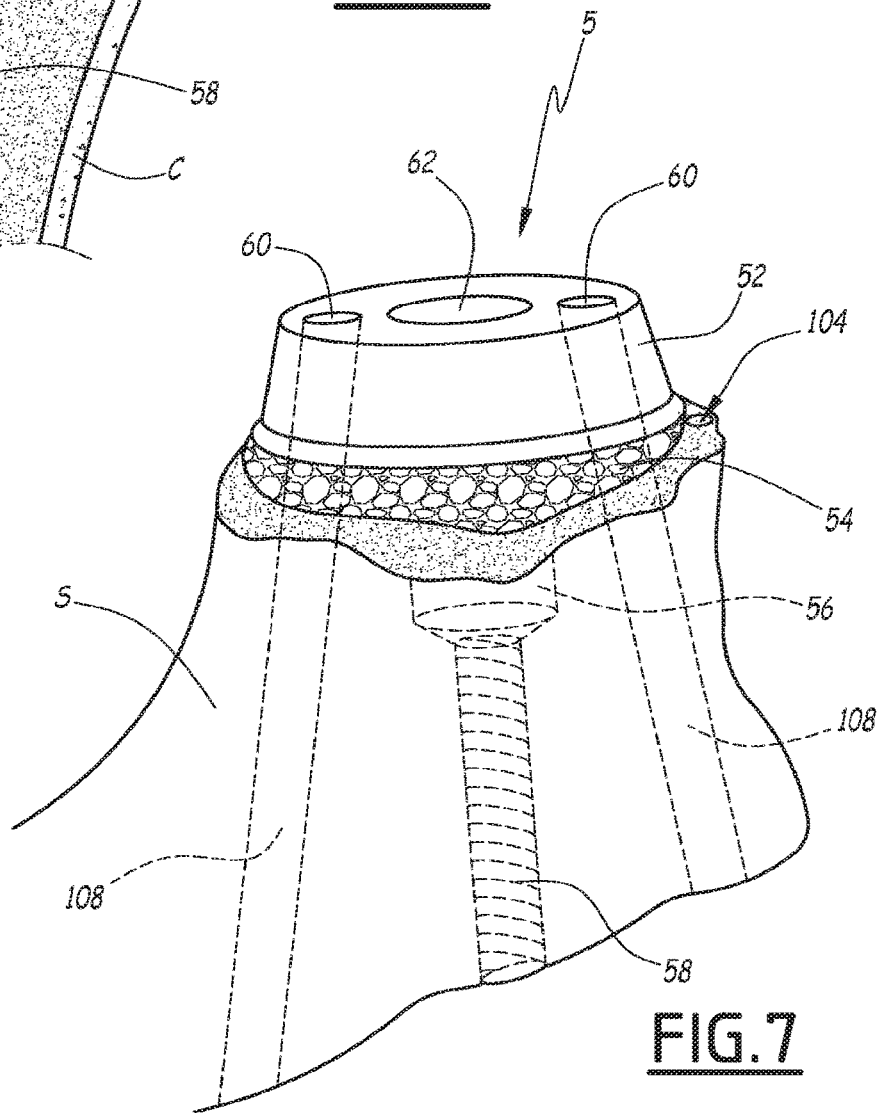
FIG. 7 is a perspective view of the scapula and shoulder implant of FIG. 6.

FIGS. 6 and 7 represent a glenoid shoulder implant 5 comprising a base plate 52 and an underside portion 54 which is made of a porous material. Said porous material may, for instance, a metallic material, a ceramic material or a polymer material, such as plasma spray, titanium trabecular structure, or acid or laser etched surface treatment. The shoulder prosthesis implant is patient specific and the underside portion 54 comprises an underside surface 54a which is congruent with the surface of the glenoid cavity G. The implant 5 comprises a post 56 extending along axis X and is adapted to receive a screw 58, which is inserted in the hole 100 to attach the implant 5 to the scapula S. The implant 5 comprises a hole 62 which runs through the base plate 52 and the underside portion 54, and which receives the screw 58.

The porous material of the underside portion 54 facilitates bone growth induced by the channels 106 in the cortical bone C. As represented on FIG. 6, cancellous bone Ca grows in the channels 106 inducing bone growth in the porosities of the underside portion 54. Such bone growth improves the anchoring of the implant 5 in the scapula S.

Once the implant 5 is attached to the scapula S, a non-shown articulation surface can be fixed to the base plate 52, using non-shown screws which are inserted in holes 60 provided in the base plate 52 and the underside portion 54. The holes 60 provide a guide for drilling the scapula S to create holes 108 for inserting the screws in the holes 60 and in the scapula S.

The surgical shoulder repair method is implemented in the following manner. The characteristics of the scapula S of the patient are first determined using imaging technology. The shape of the glenoid cavity, the density, thickness and hardness of the cortical bone C, are used to design the drilling guide 1, the underside surface 20a of the impacting device 20 and the distribution and shape of the protrusions 24, and the implant 5, including the shape of the underside surface 54a and the length of the post 56.

The glenoid cavity G is then prepared by removing, if necessary, remaining cartilage on the glenoid cavity G. The scapula S is then drilled using the drilling guide 1. The position of the drilling guide 1 is referenced using the notch 13. The glenoid cavity G is then impacted upon a one sided translational movement, using the impacting device 20 positioned using the notch 28 and guided during the translational movement by the post 22, to perforate of the cortical bone C and create channels 106 towards the cancellous bone Ca.

The patient specific implant 5 with its underside porous portion 54 and its patient specific underside surface 54a, is then attached to the scapula S using the screw 58. Bone growth in the porosities of the underside portion 54 may be accelerated using bone growth factors. The non-shown articulation surface may then be attached to the implant 5.

The drilling guide 1 and the impacting device 20 may be disposed or recycled after completion of the surgical repair process.

What is claimed is:

1. A surgical shoulder repair method comprising:
    a) providing a patient specific impacting device having an underside surface congruent with a glenoid cavity of a scapula of the patient, said underside surface being provided with protrusions adapted to perforate cortical bone of the scapula upon impact of the impacting device by a one-sided translation movement;
    b) impacting the glenoid cavity with the impacting device to create channels through the cortical bone of the scapula; and
    c) providing a patient specific shoulder implant having an underside portion made of a porous material adapted to facilitate bone growth induced by the channels created through the cortical bone, wherein
    the protrusions are arranged and shaped so that thinner and longer protrusions are used where the cortical bone is thicker.

2. The surgical shoulder repair method according to claim 1, wherein the method further comprises, prior to step a):
    d) providing a patient-specific drilling guide having an underside surface congruent with the surface of the glenoid cavity of the scapula of a patient; and
    e) drilling holes for a post of the shoulder implant and a screw for attachment of the shoulder implant.

3. The surgical shoulder repair method according to claim 2, wherein lengths of the post and the screw are predetermined.

4. The surgical shoulder repair method according to claim 2, wherein the method further comprises providing a notch in the drilling guide for placing a reference marker on the scapula.

5. The surgical shoulder repair method according to claim 2, wherein a diameter of the hole for the screw is less than a diameter of the hole for the post.

6. The surgical shoulder repair method according to claim 2, wherein the hole for the screw is coaxial with the hole for the post.

7. The surgical shoulder repair method according to claim 1, wherein a distribution and a shape of the protrusions are determined by imaging technology on a basis of bone characteristics of the glenoid cavity of the scapula of the patient.

8. The surgical shoulder repair method according to claim 7, wherein a density, a thickness, and a length of the protrusions are determined depending on a density and a thickness of the cortical bone of the glenoid cavity measured by a CT scan.

9. The surgical shoulder repair method according to claim 1, wherein the method further comprises aligning the impacting device with a reference marker provided on the scapula.

10. The surgical shoulder repair method according to claim 9, wherein the method further comprises providing a notch in the impacting device for alignment with the reference marker.

11. The surgical shoulder repair method according to claim 1, wherein a thickness of the protrusions is between 0.5 and 3 millimeters.

12. The surgical shoulder repair method according to claim 1, wherein a density of the protrusions is between 1 and 10 protrusions per square centimeter.

* * * * *